(12) United States Patent
Craig et al.

(10) Patent No.: US 7,132,586 B2
(45) Date of Patent: Nov. 7, 2006

(54) PROTEIN PRODUCTION SYSTEM

(75) Inventors: Roger Craig, Smallwood (GB); Charalambos Savakis, Heraklion (GR)

(73) Assignee: Minos Biosystems Limited, Chesire (GB)

(*) Notice: Subject to any disclaimer, the term of this patent is extended or adjusted under 35 U.S.C. 154(b) by 419 days.

(21) Appl. No.: 10/124,903

(22) Filed: Apr. 18, 2002

(65) Prior Publication Data

US 2003/0037346 A1 Feb. 20, 2003

Related U.S. Application Data

(63) Continuation of application No. PCT/GB00/04013, filed on Oct. 19, 2000.

(60) Provisional application No. 60/165,508, filed on Nov. 15, 1999.

(30) Foreign Application Priority Data

Oct. 19, 1999 (GB) ................................. 9924721.5

(51) Int. Cl.
*C12P 21/00* (2006.01)
*A01K 67/033* (2006.01)

(52) U.S. Cl. ............... 800/4; 800/5; 800/6; 800/13; 800/21; 800/25

(58) Field of Classification Search ................ 800/4, 800/5, 6, 13, 21, 25; 435/455
See application file for complete search history.

(56) References Cited

U.S. PATENT DOCUMENTS 5,614,398 A 3/1997 O'Brochta et al. ...... 435/172.3

5,840,865 A 11/1998 Savakis et al. ............. 435/196

FOREIGN PATENT DOCUMENTS

| WO | WO90/01556 | 2/1990 |
| WO | WO93/06224 | 4/1993 |
| WO | WO98/44141 | 10/1998 |

OTHER PUBLICATIONS

Minchiotti et al. "Expression of *Drosophila melanogaster* F elements in vivo," Mol. Gen. Genet. 245(2): 152-159, 1994.*
Marshall, A., "The insects are coming," Nature Biotech. 16(6): 530-533, 1998.*
Lepesant et al., "Developmentally regulated gene expression in *Drosophila* larval fat bodies," J. Mol. Appl. Genet. 1(5): 371-383, 1982.*
Antoniewski, et al. (1995), *Characterization of an EcR/USP Heterodimer Target Site that Mediates Ecdysone Responsiveness of the Drosophila Lsp-2 Gene*. Mol. Gen. Genet. 249:545-556.
Heinrich, J. & Scott, M. (2000), *A Repressible Female-Specific Lethal Genetic System for Making Transgenic Insect Strains Suitable for a Sterile-Release Program*. PNAS. 97(15):8229-8232.
Huynh, C. & Zieler, H. (1999), *Construction of Modular and Versatile Plasmid Vectors for the High-Level Expression of Single or Multiple Genes in Insects and Insect Cell Lines*. J. Mol. Biol. 288:13-20.

(Continued)

*Primary Examiner*—Scott D. Priebe
(74) *Attorney, Agent, or Firm*—Elizabeth N. Spar; Kathleen M. Williams; Edwards Angell Palmer & Dodge LLP

(57) ABSTRACT

The invention relates to a method for producing a protein of interest comprising transforming a target insect with a non-viral expression system that expresses the protein in the insect larvae, breeding the insect to produce larvae, culturing the larvae and isolating the protein from the larvae.

21 Claims, 10 Drawing Sheets

OTHER PUBLICATIONS

Jowett, et al. (1991), *Mammalian genes expressed in Drosophila: A transgenic model for the study of mechanisms of chemical mutagenesis and metabolism.* EMBO Journ. v. 10(5):1075-1081.

Loukeris, et al. (1995), *Introduction of the Transposable Element Minos into the Germ Line of Drosophila melanogaster.* PNAS USA. 92:9485-9489.

Loukeris, et al. (1995), *Gene Transfer into the Medfly, Ceratitis capitata, with a Drosophila hydei Transposable Element.* Science. 270:2002-2005.

Papadimitriou, et al. (1998), *The Heat Shock 70 Gene Family in the Mediterranean Fruit Fly Ceratitis capitata.* Insect Mol. Biol. 7(3):279-290.

Pham, et al. (1999), *Human Interleukin-2 Production in Insect (Trichoplusa ni) Larvae: Effects and Partial Control of Proteolysis.* Biotech. & Bioleng. 62(2):175-182.

Plasterk, et al. (1999), *Resident Aliens: The tcl/mariner superfamily of transposable elements.* TIG. 15(8):326-332.

Qin, et al. (1994), *Recombination of Human Macrophage Colony Stimulating Factor by Domestic Silkworm Gene Engineering.* Univ. Nanjing / Accession No. 1997-193471[18]. (TRANSLATED).

Rancourt, et al. (1991), *Differential translatability of antifreeze protein mRNAs in a Transgenic Host.* Biochimica et Biophysica Acta., 1129:189-194.

Umapathysivam, et al. (2000), *Determination of Acid a-Glucosidease Protein: Evaluation as a Screening Marker for Pompe Disease and Other Lysosomal Storage Disorders.* Clin. Chem. 46(9):1318-1325.

International Search Report for PCT/GB00/04013.

* cited by examiner

| FIG. 8A |
|---|
| FIG. 8B |
| FIG. 8C |

FIG. 8

```
1   AAATTCTATTTCAAGGAGACAGTCATAATGAAATACCTATTGCCTACGGCAGCCGCTGGA
1    K  F  Y  F  K  E  T  V  I  M  K  Y  L  L  P  T  A  A  G
1    N  S  I  S  R  R  Q  S  *  *  N  T  Y  C  L  R  Q  P  L  D
1    I  L  F  Q  G  D  S  H  N  E  I  P  I  A  Y  G  S  R  W  I

61  TTGTTATTACTCGCGGCCCAGCCGGCCATGGCCCAGGTGCAGCTGCAGGAGTCCGGGGGA
21   L  L  L  L  A  A  Q  P  A  M  A  Q  V  Q  L  Q  E  S  G  G
21   C  Y  S  R  P  S  R  P  W  P  R  C  S  C  R  S  P  G  E
21   V  I  T  R  G  P  A  G  H  G  P  G  A  A  A  G  V  R  G  R
```

FIG. 8A

```
121  GGCTCGGTGCAGCCTGGGGGTTCTCTGAGACTCTCCTGTGTAGTCTCTGGACTCTCACGCCG
 41   G  S  V  Q  P  G  G  S  L  R  L  S  C  V  V  S  G  L  T  P
 41   A  R  C  S  L  G  V  L  *  D  S  P  V  *  S  L  D  S  R  R
 41   L  G  A  A  W  G  F  S  E  T  L  L  C  S  L  W  T  H  A  G

181  GGCTATGATTCCATAGGCTGGTTCCGCCAGGCCCCAGGGAAGGAGCGCGAGGAGTCTCT
 61   G  Y  D  S  I  G  W  F  R  Q  A  P  G  K  E  R  E  G  V  S
 61   A  M  I  P  *  A  G  S  A  R  P  Q  G  R  S  A  R  E  S  L
 61   L  *  F  H  R  L  V  P  P  G  P  R  E  G  A  R  G  S  L  C

241  GCTATTAGTCTCGGGGGTGCCACTTACTATGCAGACTCCGTGAAGGGCCGCTTCACC
 81   A  I  S  L  G  G  G  A  T  Y  Y  A  D  S  V  K  G  R  F  T
 81   L  L  V  S  A  A  V  P  L  T  M  Q  T  P  *  R  A  A  S  P
 81   Y  *  S  R  R  R  C  H  L  L  C  R  L  R  E  G  P  L  H  H

301  ATCTCCAAAAACAACGCCAAGACGACGGTGTATCTGCAAATGAACAGCCTGAACCCTGAC
101   I  S  K  N  N  A  K  T  T  V  Y  L  Q  M  N  S  L  N  P  D
101   S  P  K  T  T  P  R  R  R  C  I  C  K  *  T  A  *  T  L  T
101   L  Q  K  Q  R  Q  D  D  G  V  S  A  N  E  Q  P  E  P  *  R
```

FIG. 8B

```
361  GACACGGCCCGTTATTACTGTGTGCCATGGGCAGGTGGAGGTGGAGGGCGCCCTACTGGGGCCAG
121   D  T  A  V  Y  Y  C  A  M  G  R  W  R  A  P  Y  W  G  Q
121   T  R  P  F  I  T  V  L  P  W  G  G  G  G  R  R  T  G  A  R
121   H  G  R  L  L  L  C  C  H  G  E  V  E  G  A  V  L  G  P  G

421  GGGACCCTGGTCACGGTCTCCTCAGCGCACCACAGCGAAGACCCCAGTCCGGCGGCC
141   G  T  L  V  T  V  S  S  A  H  H  S  E  D  P  S  S  A  A  A
141   G  P  W  S  R  S  P  Q  R  T  T  A  K  T  P  A  P  R  P  P
141   D  P  G  H  G  L  L  S  A  P  Q  R  R  P  Q  L  R  G  R  P

481  CATCACCATCACCATCACGGGGCCGCAGAACAAAACTCATCTCAGAAGAGGATCTGAAT
161   H  H  H  H  H  H  G  A  A  E  Q  K  L  I  S  E  E  D  L  N
161   I  T  I  T  I  T  G  P  Q  N  K  N  S  Q  K  R  I  *  M
161   S  P  S  P  S  R  G  R  R  T  K  T  H  L  R  R  G  S  E  W

541  GGGGCCGCATAGACTGTTGAAAGTTGTTTAGCAAAACCTCATACAGAAAATTCATTTACT
181   G  A  A  *  T  V  E  S  C  L  A  K  P  H  T  E  N  S  F  T
181   G  P  H  R  L  L  K  V  V  *  Q  N  L  I  Q  K  I  H  L  L
181   G  R  I  D  C  *  K  L  F  S  K  T  S  Y  R  K  F  I  Y  *

601  AACGTCTGGAAAGGCGACAAAACTTTAGATCGTTACGCTAACTATGAGGGCTGTCTGTGGA
```

FIG. 8C

SEQUENCE LISTING

<160> NUMBER OF SEQ ID NOS: 19

<210> SEQ ID NO 1
<211> LENGTH: 660
<212> TYPE: DNA
<213> ORGANISM: camel
<220> FEATURE:
<221> NAME/KEY: CDS
<222> LOCATION: (1)..(600)
<223> OTHER INFORMATION:

<400> SEQUENCE: 1

```
aaa ttc tat ttc aag gag aca gtc ata atg aaa tac cta ttg cct acg        48
Lys Phe Tyr Phe Lys Glu Thr Val Ile Met Lys Tyr Leu Leu Pro Thr
1               5                   10                  15 gca gcc gct gga ttg tta tta ctc gcg gcc cag ccg gcc atg gcc cag        96
Ala Ala Ala Gly Leu Leu Leu Leu Ala Ala Gln Pro Ala Met Ala Gln
            20                  25                  30 gtg cag ctg cag gag tcc ggg gga ggc tcg gtg cag cct ggg ggt tct       144
Val Gln Leu Gln Glu Ser Gly Gly Gly Ser Val Gln Pro Gly Gly Ser
        35                  40                  45 ctg aga ctc tcc tgt gta gtc tct gga ctc acg ccg ggc tat gat tcc       192
Leu Arg Leu Ser Cys Val Val Ser Gly Leu Thr Pro Gly Tyr Asp Ser
    50                  55                  60 ata ggc tgg ttc cgc cag gcc cca ggg aag gag cgc gag gga gtc tct       240
Ile Gly Trp Phe Arg Gln Ala Pro Gly Lys Glu Arg Glu Gly Val Ser
65                  70                  75                  80 gct att agt ctc ggc ggc ggt gcc act tac tat gca gac tcc gtg aag       288
Ala Ile Ser Leu Gly Gly Gly Ala Thr Tyr Tyr Ala Asp Ser Val Lys
                85                  90                  95 ggc cgc ttc acc atc tcc aaa aac aac gcc aag acg acg gtg tat ctg       336
Gly Arg Phe Thr Ile Ser Lys Asn Asn Ala Lys Thr Thr Val Tyr Leu
            100                 105                 110 caa atg aac agc ctg aac cct gac gac acg gcc gtt tat tac tgt gct       384
Gln Met Asn Ser Leu Asn Pro Asp Asp Thr Ala Val Tyr Tyr Cys Ala
        115                 120                 125 gcc atg ggg agg tgg agg gcg ccg tac tgg ggc cag ggg acc ctg gtc       432
Ala Met Gly Arg Trp Arg Ala Pro Tyr Trp Gly Gln Gly Thr Leu Val
130                 135                 140 acg gtc tcc tca gcg cac cac agc gaa gac ccc agc tcc gcg gcc gcc       480
Thr Val Ser Ser Ala His His Ser Glu Asp Pro Ser Ser Ala Ala Ala
145                 150                 155                 160 cat cac cat cac cat cac ggg gcc gca gaa caa aaa ctc atc tca gaa       528
His His His His His His Gly Ala Ala Glu Gln Lys Leu Ile Ser Glu
                165                 170                 175 gag gat ctg aat ggg gcc gca tag act gtt gaa agt tgt tta gca aaa       576
Glu Asp Leu Asn Gly Ala Ala     Thr Val Glu Ser Cys Leu Ala Lys
            180                 185                 190 cct cat aca gaa aat tca ttt act aacgtctgga aagcgacaaa actttagatc     630
Pro His Thr Glu Asn Ser Phe Thr
            195 gttacgctaa ctatgagggc tgtctgtgga                                      660
```

<210> SEQ ID NO 2
<211> LENGTH: 183
<212> TYPE: PRT
<213> ORGANISM: camel

<400> SEQUENCE: 2

Lys Phe Tyr Phe Lys Glu Thr Val Ile Met Lys Tyr Leu Leu Pro Thr
1               5                   10                  15

Ala Ala Ala Gly Leu Leu Leu Ala Ala Gln Pro Ala Met Ala Gln
            20                  25                  30

Val Gln Leu Gln Glu Ser Gly Gly Ser Val Gln Pro Gly Gly Ser
    35                  40                  45

Leu Arg Leu Ser Cys Val Val Ser Gly Leu Thr Pro Gly Tyr Asp Ser
    50                  55                  60

Ile Gly Trp Phe Arg Gln Ala Pro Gly Lys Glu Arg Glu Gly Val Ser
65                  70                  75                  80

Ala Ile Ser Leu Gly Gly Ala Thr Tyr Tyr Ala Asp Ser Val Lys
                85                  90                  95

Gly Arg Phe Thr Ile Ser Lys Asn Asn Ala Lys Thr Thr Val Tyr Leu
            100                 105                 110

Gln Met Asn Ser Leu Asn Pro Asp Asp Thr Ala Val Tyr Tyr Cys Ala
        115                 120                 125

Ala Met Gly Arg Trp Arg Ala Pro Tyr Trp Gly Gln Gly Thr Leu Val
    130                 135                 140

Thr Val Ser Ser Ala His His Ser Glu Asp Pro Ser Ser Ala Ala Ala
145                 150                 155                 160

His His His His His His Gly Ala Ala Glu Gln Lys Leu Ile Ser Glu
                165                 170                 175

Glu Asp Leu Asn Gly Ala Ala
            180

<210> SEQ ID NO 3
<211> LENGTH: 16
<212> TYPE: PRT
<213> ORGANISM: camel

<400> SEQUENCE: 3

Thr Val Glu Ser Cys Leu Ala Lys Pro His Thr Glu Asn Ser Phe Thr
1               5                   10                  15

<210> SEQ ID NO 4
<211> LENGTH: 659
<212> TYPE: DNA
<213> ORGANISM: camel
<220> FEATURE:
<221> NAME/KEY: CDS
<222> LOCATION: (1)..(600)
<223> OTHER INFORMATION:

<400> SEQUENCE: 4 aat tct att tca agg aga cag tca taa tga aat acc tat tgc cta cgg          48
Asn Ser Ile Ser Arg Arg Gln Ser         Asn Thr Tyr Cys Leu Arg
1               5                           10 cag ccg ctg gat tgt tat tac tcg cgg ccc agc cgg cca tgg ccc agg          96
Gln Pro Leu Asp Cys Tyr Tyr Ser Arg Pro Ser Arg Pro Trp Pro Arg
15                  20                  25                  30 tgc agc tgc agg agt ccg ggg gag gct cgg tgc agc ctg ggg gtt ctc         144
Cys Ser Cys Arg Ser Pro Gly Glu Ala Arg Cys Ser Leu Gly Val Leu
                35                  40                  45

```
tga gac tct cct gtg tag tct ctg gac tca cgc cgg gct atg att cca        192
    Asp Ser Pro Val     Ser Leu Asp Ser Arg Arg Ala Met Ile Pro
                50                      55                      60 tag gct ggt tcc gcc agg ccc cag gga agg agc gcg agg gag tct ctg        240
    Ala Gly Ser Ala Arg Pro Gln Gly Arg Ser Ala Arg Glu Ser Leu
                65              70                      75 cta tta gtc tcg gcg gcg gtg cca ctt act atg cag act ccg tga agg        288
Leu Leu Val Ser Ala Ala Val Pro Leu Thr Met Gln Thr Pro     Arg
                80              85                          90 gcc gct tca cca tct cca aaa aca acg cca aga cga cgg tgt atc tgc        336
Ala Ala Ser Pro Ser Pro Lys Thr Thr Pro Arg Arg Arg Cys Ile Cys
                95              100                     105 aaa tga aca gcc tga acc ctg acg aca cgg ccg ttt att act gtg ctg        384
Lys     Thr Ala     Thr Leu Thr Thr Arg Pro Phe Ile Thr Val Leu
                    110             115                     120 cca tgg gga ggt gga ggg cgc cgt act ggg gcc agg gga ccc tgg tca        432
Pro Trp Gly Gly Gly Gly Arg Arg Thr Gly Ala Arg Gly Pro Trp Ser
                125             130                     135 cgg tct cct cag cgc acc aca gcg aag acc cca gct ccg cgg ccg ccc        480
Arg Ser Pro Gln Arg Thr Thr Ala Lys Thr Pro Ala Pro Arg Pro Pro
                140             145                     150 atc acc atc acc atc acg ggg ccg cag aac aaa aac tca tct cag aag        528
Ile Thr Ile Thr Ile Thr Gly Pro Gln Asn Lys Asn Ser Ser Gln Lys
                155             160                     165 agg atc tga atg ggg ccg cat aga ctg ttg aaa gtt gtt tag caa aac        576
Arg Ile     Met Gly Pro His Arg Leu Leu Lys Val Val     Gln Asn
    170             175                     180 ctc ata cag aaa att cat tta cta acgtctggaa agcgacaaaa ctttagatcg       630
Leu Ile Gln Lys Ile His Leu Leu
        185             190 ttacgctaac tatgagggct gtctgtgga                                        659

<210> SEQ ID NO 5
<211> LENGTH: 8
<212> TYPE: PRT
<213> ORGANISM: camel

<400> SEQUENCE: 5

Asn Ser Ile Ser Arg Arg Gln Ser
1               5

<210> SEQ ID NO 6
<211> LENGTH: 38
<212> TYPE: PRT
<213> ORGANISM: camel

<400> SEQUENCE: 6

Asn Thr Tyr Cys Leu Arg Gln Pro Leu Asp Cys Tyr Tyr Ser Arg Pro
1               5                   10                  15

Ser Arg Pro Trp Pro Arg Cys Ser Cys Arg Ser Pro Gly Glu Ala Arg
                20                  25                  30

Cys Ser Leu Gly Val Leu
            35

<210> SEQ ID NO 7
<211> LENGTH: 4
<212> TYPE: PRT
<213> ORGANISM: camel

<400> SEQUENCE: 7

Asp Ser Pro Val
```

```
<210> SEQ ID NO 8
<211> LENGTH: 10
<212> TYPE: PRT
<213> ORGANISM: camel

<400> SEQUENCE: 8

Ser Leu Asp Ser Arg Arg Ala Met Ile Pro
1               5                   10

<210> SEQ ID NO 9
<211> LENGTH: 29
<212> TYPE: PRT
<213> ORGANISM: camel

<400> SEQUENCE: 9

Ala Gly Ser Ala Arg Pro Gln Gly Arg Ser Ala Arg Glu Ser Leu Leu
1               5                   10                  15

Leu Val Ser Ala Ala Val Pro Leu Thr Met Gln Thr Pro
            20                  25

<210> SEQ ID NO 10
<211> LENGTH: 18
<212> TYPE: PRT
<213> ORGANISM: camel

<400> SEQUENCE: 10

Arg Ala Ala Ser Pro Ser Pro Lys Thr Thr Pro Arg Arg Arg Cys Ile
1               5                   10                  15

Cys Lys

<210> SEQ ID NO 11
<211> LENGTH: 61
<212> TYPE: PRT
<213> ORGANISM: camel

<400> SEQUENCE: 11

Thr Leu Thr Thr Arg Pro Phe Ile Thr Val Leu Pro Trp Gly Gly Gly
1               5                   10                  15

Gly Arg Arg Thr Gly Ala Arg Gly Pro Trp Ser Arg Ser Pro Gln Arg
            20                  25                  30

Thr Thr Ala Lys Thr Pro Ala Pro Arg Pro Pro Ile Thr Ile Thr Ile
        35                  40                  45

Thr Gly Pro Gln Asn Lys Asn Ser Ser Gln Lys Arg Ile
    50                  55                  60

<210> SEQ ID NO 12
<211> LENGTH: 10
<212> TYPE: PRT
<213> ORGANISM: camel

<400> SEQUENCE: 12

Met Gly Pro His Arg Leu Leu Lys Val Val
1               5                   10

<210> SEQ ID NO 13
<211> LENGTH: 10
<212> TYPE: PRT
<213> ORGANISM: camel

<400> SEQUENCE: 13
```

```
Gln Asn Leu Ile Gln Lys Ile His Leu Leu
1               5                   10
```

<210> SEQ ID NO 14
<211> LENGTH: 658
<212> TYPE: DNA
<213> ORGANISM: camel
<220> FEATURE:
<221> NAME/KEY: CDS
<222> LOCATION: (1)..(600)
<223> OTHER INFORMATION:

<400> SEQUENCE: 14

```
att cta ttt caa gga gac agt cat aat gaa ata cct att gcc tac ggc      48
Ile Leu Phe Gln Gly Asp Ser His Asn Glu Ile Pro Ile Ala Tyr Gly
1               5                   10                  15 agc cgc tgg att gtt att act cgc ggc cca gcc ggc cat ggc cca ggt      96
Ser Arg Trp Ile Val Ile Thr Arg Gly Pro Ala Gly His Gly Pro Gly
                20                  25                  30 gca gct gca gga gtc cgg ggg agg ctc ggt gca gcc tgg ggg ttc tct     144
Ala Ala Ala Gly Val Arg Gly Arg Leu Gly Ala Ala Trp Gly Phe Ser
            35                  40                  45 gag act ctc ctg tgt agt ctc tgg act cac gcc ggg cta tga ttc cat     192
Glu Thr Leu Leu Cys Ser Leu Trp Thr His Ala Gly Leu     Phe His
50                  55                  60 agg ctg gtt ccg cca ggc ccc agg gaa gga gcg cga ggg agt ctc tgc     240
Arg Leu Val Pro Pro Gly Pro Arg Glu Gly Ala Arg Gly Ser Leu Cys
    65                  70                  75 tat tag tct cgg cgg cgg tgc cac tta cta tgc aga ctc cgt gaa ggg     288
Tyr     Ser Arg Arg Arg Cys His Leu Leu Cys Arg Leu Arg Glu Gly
80                  85                      90 ccg ctt cac cat ctc caa aaa caa cgc caa gac gac ggt gta tct gca     336
Pro Leu His His Leu Gln Lys Gln Arg Gln Asp Asp Gly Val Ser Ala
95                  100                 105                 110 aat gaa cag cct gaa ccc tga cga cac ggc cgt tta tta ctg tgc tgc     384
Asn Glu Gln Pro Glu Pro     Arg His Gly Arg Leu Leu Leu Cys Cys
                115                     120                 125 cat ggg gag gtg gag ggc gcc gta ctg ggg cca ggg gac cct ggt cac     432
His Gly Glu Val Glu Gly Ala Val Leu Gly Pro Gly Asp Pro Gly His
                130                 135                 140 ggt ctc ctc agc gca cca cag cga aga ccc cag ctc cgc ggc cgc cca     480
Gly Leu Leu Ser Ala Pro Gln Arg Arg Pro Gln Leu Arg Gly Arg Pro
                145                 150                 155 tca cca tca cca tca cgg ggc cgc aga aca aaa act cat ctc aga aga     528
Ser Pro Ser Pro Ser Arg Gly Arg Arg Thr Lys Thr His Leu Arg Arg
            160                 165                 170 gga tct gaa tgg ggc cgc ata gac tgt tga aag ttg ttt agc aaa acc     576
Gly Ser Glu Trp Gly Arg Ile Asp Cys     Lys Leu Phe Ser Lys Thr
            175                 180                 185 tca tac aga aaa ttc att tac taa cgtctggaaa gcgacaaaac tttagatcgt    630
Ser Tyr Arg Lys Phe Ile Tyr
            190                 195 tacgctaact atgagggctg tctgtgga                                      658
```

<210> SEQ ID NO 15
<211> LENGTH: 61
<212> TYPE: PRT
<213> ORGANISM: camel

<400> SEQUENCE: 15

```
Ile Leu Phe Gln Gly Asp Ser His Asn Glu Ile Pro Ile Ala Tyr Gly
1               5                   10                  15
```

Ser Arg Trp Ile Val Ile Thr Arg Gly Pro Ala Gly His Gly Pro Gly
            20                  25                  30

Ala Ala Ala Gly Val Arg Gly Arg Leu Gly Ala Ala Trp Gly Phe Ser
        35                  40                  45

Glu Thr Leu Leu Cys Ser Leu Trp Thr His Ala Gly Leu
    50                  55                  60

<210> SEQ ID NO 16
<211> LENGTH: 19
<212> TYPE: PRT
<213> ORGANISM: camel

<400> SEQUENCE: 16

Phe His Arg Leu Val Pro Gly Pro Arg Glu Gly Ala Arg Gly Ser
1               5                   10                  15

Leu Cys Tyr

<210> SEQ ID NO 17
<211> LENGTH: 36
<212> TYPE: PRT
<213> ORGANISM: camel

<400> SEQUENCE: 17

Ser Arg Arg Arg Cys His Leu Leu Cys Arg Leu Arg Glu Gly Pro Leu
1               5                   10                  15

His His Leu Gln Lys Gln Arg Gln Asp Asp Gly Val Ser Ala Asn Glu
            20                  25                  30

Gln Pro Glu Pro
        35

<210> SEQ ID NO 18
<211> LENGTH: 66
<212> TYPE: PRT
<213> ORGANISM: camel

<400> SEQUENCE: 18

Arg His Gly Arg Leu Leu Cys Cys His Gly Glu Val Glu Gly Ala
1               5                   10                  15

Val Leu Gly Pro Gly Asp Pro Gly His Gly Leu Leu Ser Ala Pro Gln
            20                  25                  30

Arg Arg Pro Gln Leu Arg Gly Arg Pro Ser Pro Ser Pro Ser Arg Gly
        35                  40                  45

Arg Arg Thr Lys Thr His Leu Arg Arg Gly Ser Glu Trp Gly Arg Ile
    50                  55                  60

Asp Cys
65

<210> SEQ ID NO 19
<211> LENGTH: 13
<212> TYPE: PRT
<213> ORGANISM: camel

<400> SEQUENCE: 19

Lys Leu Phe Ser Lys Thr Ser Tyr Arg Lys Phe Ile Tyr
1               5                   10

PROTEIN PRODUCTION SYSTEM

RELATED APPLICATIONS

The present application is a continuation of PCT/GB00/04013, filed on Oct. 19, 2000 and claims priority to GB application Ser. No. 9924721.5, filed Oct. 19, 1999, and U.S. application Ser. No. 60/165,508, filed Nov. 15, 1999.

TECHNICAL FIELD OF THE INVENTION

The invention is related to protein production systems in insect larvae.

BACKGROUND OF THE INVENTION

The present invention relates to a system for the production of proteins in insect larvae. In particular, the invention encompasses the production of proteins of interest in *Drosophila* and Medfly larvae.

Protein production systems, in which polypeptides or proteins of interest are produced in recombinant organisms or cells, are the backbone of commercial biotechnology. The earliest systems, based on bacterial expression in hosts such as *E. coli*, have been joined by systems based on eukaryotic hosts, in particular mammalian cells in culture, insect cells both in culture and in the form of whole insects, and transgenic mammals such as sheep and goats.

Prokaryotic cell culture systems are easy to maintain and cheap to operate. However, prokaryotic cells are not capable of post-translational modification of eukaryotic proteins. Moreover, many proteins are incorrectly folded, requiring specific procedures to refold them, which adds to the cost of production.

Eukaryotic cell culture systems have been described for a number of applications. For example, mammalian cells are capable of post-translational modification, and generally produce proteins which are correctly folded and soluble. The chief disadvantages of mammalian cell systems include the requirement for specialised and expensive culture facilities, and the risk of infection, which can lead to loss of the whole culture.

Plant production systems may be used for protein expression, and may achieve high-yield production. However, transgenic plants crops are difficult to contain, raising the risk of contamination of the environment with genetically manipulated material.

Insect cells are also used for polypeptide expression. The most widespread expression system used in insect cells is based on baculovirus vectors. A baculovirus expression vector is constructed by replacing the polyhedrin gene of baculovirus, which encodes a major structural protein of the baculovirus, with a heterologous gene, under the control of the strong native polyhedrin promoter. Cultured insect host cells are infected with the recombinant virus, and the protein produced thereby can be recovered from the cells themselves or from the culture medium if suitable secretion signals are employed. These systems also, however, suffer from problems associated with infection of the culture and the requirement for specialised culture facilities.

Organism based expression systems avoid many of the infection disadvantages and are easier to grow than cell cultures. For instance, the use of virus vectors such as baculovirus allows infection of entire insects, which have fewer requirements for special growth conditions. Large insects, such as silk moths, provide a high yield of heterologous protein. The protein can be extracted from the insects according to conventional extraction techniques.

Also known are techniques based on expression of proteins of interest in mammals such as goats and sheep, under the control of milk protein expression control sequences such that they are expressed in milk: Such techniques have great potential advantages, but are expensive due to the requirement for isolation of endogenous mammalian viruses, prions and proteins from the final product. Moreover, the cost of generating and keeping large transgenic animals is high.

The use of insect larvae, those of *Trichoplusa ni*, have been proposed for use in protein production systems (Pham et al., 1999 Biotech Bioeng 62:175–182). However, such systems have only been suggested in combination with viral vector technology based around baculoviruses.

Where proteins are intended for dietary or pharmaceutical use, the use of bacterial systems and/or viral vectors is undesirable. There is therefore a requirement in the art for a protein production system which is both robust and scaleable, as whole organism based systems are, and free from virus-based vectors, as well as inexpensive to operate in a contained environment.

SUMMARY OF THE INVENTION

According to a first aspect, the present invention provides a method for producing a protein of interest, comprising:
(a) transforming an insect with a non-viral expression system capable of expressing the protein of interest in the larvae of the insect;
(b) breeding the insect to produce larvae;
(c) culturing the larvae; and
(d) isolating the protein of interest from the larvae.

The method according to the present invention allows the rapid production of milligram quantities of polypeptides for research purposes, the production of kilogram quantities of proteins for clinical and diagnostic applications and potentially thousands of kilograms of industrial enzymes at low cost, due to the ease with which insect larvae may be cultured using established culture techniques.

The advantages of methods according to the invention are manifold. Mass rearing of insect larvae is possible using existing technology and permits the production of polypeptide products at extremely low cost, in a controlled production environment. This facilitates regulatory approval with respect to whole organisms such as mammals, where the absence of viruses and prions must be proven before approval is given. Moreover, the method of the invention avoids the disadvantages associated with animal (including insect) cell culture, which include the higher risk of infection, and the risk of viral or prion contamination in the case of mammalian cell culture or transgenic production systems.

The term "protein" includes single-chain polypeptide molecules as well as multiple-polypeptide complexes where individual constituent polypeptides are linked by covalent or non-covalent means. The term "polypeptide" includes peptides of two or more amino acids in length, typically having more than 5, 10 or 20 amino acids.

A non-viral expression system, as referred to herein, includes any technique for transforming insects which is not based on a virus such as baculovirus. For example, non-viral expression systems include those based on autonomously replicating plasmids, integrating plasmids and transposon-based systems. The preferred expression system for use in insect larvae is based on transposons. Suitable transposons are described in more detail below.

The expression system used in the method of the invention comprises control elements which are active in insect cells, and particularly in insect larvae. Many insect control sequences, including various promoters, are active in a number of diverse species. Therefore, it is not essential that sequences derived from the insect in question be used. Inducible or constitutively active sequences may be used.

Preferably, the control sequences are inducible sequences. A preferred inducible promoter is the heat shock protein HSP70 promoter, which is induced by increasing the temperature at which the larvae are cultured, and tetracycline-inducible expression systems (Heinrich and Scott, PNAS 97:8229–8232, 2000).

In order to increase protein production, multiple expression systems may be used. These systems may be arranged with two or more coding sequences present in each system, or as multiple single systems. In either case, a balancer chromosome may be used in order to favour expression system retention and transmission to progeny during insect crossing.

An advantage of insect larval culture is that the cultures can be synchronised, such that all larvae reach the same level of maturity at the same time. This can be achieved by varying the culture temperature, since larvae develop more slowly at lower temperatures. For example, at 18° C., larvae develop at half the rate compared to growth at 25° C.

Further advantages of the invention include the fact that protein accumulation may be directed to the fat body, or the protein may be secreted into the haemolymph under the control of suitable control regions and signal peptides, such as the larval serum protein sequences.

BRIEF DESCRIPTION OF THE FIGURES

FIG. 8 is a prelimianry sequence of an anti-PERV p30 antibody clone isolated from a camelid antibody library and expressed in medfly larvae.

DETAILED DESCRIPTION OF THE INVENTION

Figure 1:
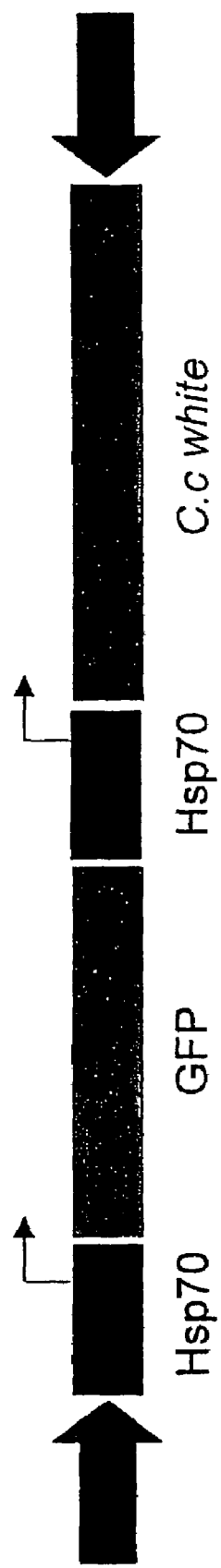
FIG. 1 shows the structure of the pMiHspGFP/HspCcW transposon, which expresses GFP and the white gene under the control of the Hsp70 promoter.

Although in general the techniques mentioned herein are well known in the art, reference may be made in particular to Sambrook et al., Molecular Cloning, A Laboratory Manual (1989) and Ausubel et al., Short Protocols in Molecular Biology (1999)$4^{th}$ Ed. John Wiley & Sons, Inc.

Transposons

Transposons are genetic elements which are capable of "jumping" or transposing from one position to another within the genome of a species. They are widely distributed amongst animals, including insects.

Transposons are active within their host species due to the activity of a transposase protein encoded by the elements themselves, or provided by other means—such as by injection of transposase-encoding mRNA, the use of a second coding sequence encoding transposase or the addition of transposase protein itself. Advances in the understanding of the mechanisms of transposition have resulted in the development of genetic tools based on transposons which can be used for gene transfer.

Any transposable element active in the desired insect may be used. Preferably, however, the transposable element is selected from the group consisting of Minos, mariner, Hermes, Sleeping Beauty and piggyBac.

Minos is a transposable element which is active in Medfly. It is described in U.S. Pat. No. 5,840,865, which is incorporated herein by reference in its entirety. The use of Minos to transform insects is described in the foregoing US patent.

Mariner is a transposon originally isolated from Drosophila, but since discovered in several invertebrate and vertebrate species. The use of mariner to transform organisms is described in International patent application WO99/09817.

Hermes is derived from the common housefly. Its use in creating transgenic insects is described in U.S. Pat. No. 5,614,398 incorporated herein by reference in its entirety.

PiggyBac is a transposon derived from the baculovirus host Trichoplusia ni. Its use for germ-line transformation of Medfly has been described by Handler et al., (1998) PNAS (USA) 95:7520–5.

Gene transfer is performed by proven transposon-mediated germ line transformation. The transposon of choice is Minos, which has been shown to function as a transgenesis vector in medfly (Loukeris et al., 1995) and Drosophila. Other transposons that are functional in medfly, such as piggyBac (McCombs et al., 1998) and can be used as alternatives. Medfly transformation methodology is well described in the literature (Loukeris et al. 1995). Briefly, circular plasmid DNA containing a transposon consisting of a gene of interest (such as erythropoietin, plus appropriate regulatory DNA sequences) flanked by the two transposon ends is co-injected into pre-blastoderm medfly embryos along with a source of transposase (a plasmid expressing transposase, in vitro-synthesised mRNA encoding transposase, or the transposase protein itself). In the early embryos transposase interacts with the transposon ends and catalyses excision of the transposon and reintegration into chromosomes at random positions. Usually, to facilitate detection of transgenic flies, a "marker gene", such as a gene that confers a dominant, visible or otherwise selectable phenotype, is also included in the transposon. Transgenic flies are detected among the progeny of the injected flies using the marker gene phenotype and then bred to homozygosity. Several such strains, each containing an insertion at a different position in the genome, can be produced in each transformation experiment involving injection of several hundred eggs.

Multiple Insertions

In order to increase the levels of expression, strains containing multiple insertions can be constructed by interbreeding different transgenic strains. This procedure can be facilitated by the use of balancer chromosomes. Balancer chromosomes contain several overlapping inversions, one or more recessive lethal mutations and at least one dominant visible mutation. These chromosomes suppress recombination and can be used to keep and manipulate chromosomes carrying several mutant genes. A medfly balancer chromosome, FiM 1, has been described. By suppressing recombination over a large region of chromosome 5; it can be used for construction of a chromosome 5 carrying several transposon insertions.

Choice of Insect and Promoter

A number of insect larvae would be suitable for use in the present invention, including any one of *Bactrocera oleae* (olive fly), *Bactrocera orientalis* (oriental fruit fly). *Heliothis armigera* (cotton bollworm), *Trichoplusa ni* (cabbage looper). *Manduca sexta* (tobacco hornworm), *Lobesia botrana* (grapevine moth), *Anopheles gambiae* (mosquito). *Aedes aegypti* (yellow fever mosquito), *Glossina morsitans* (tse-tse fly), *Simulium* sp. (black fly), *Phlebotomus* sp. (sand fly), *Musca domestica* (house fly) and *Ceratitis capitata* (Medfly). Preferred, however, is the medfly.

Preferably, the promoter used is a strong promoter. Two alternative categories of promoter are available for use: inducible and constitutive promoters.

Inducible promoters include, for example, heat shock promoters. Preferably, the heat shock promoter is an insect heat shock promoter, for example the *Drosophila melanogaster* hsp70 promoter, which is capable of driving the expression of genes in heterologous organisms, including medfly. The invention also encompasses the use of the medfly hsp70 promoter (Papadimitriou et al., (1998) Insect Mol Biol 7:279–90). Alternative systems may be based on induction with the antibiotic tatracycline (Heinrich and Scott, PNAS 97:8229–8232, 2000).

Heat shock promoters are inducible by raising the temperature of the conditions under which the medfly are being cultured. For example, at 23–25° C., the hsp70 promoter is active at low levels or not at all. This allows the insect larva to develop without stress induced by the production of a heterologous protein. At higher temperatures, however, such as 37–42° C., the hsp70 promoter is induced and expresses the heterologous protein at a high level.

Inducible promoters may be constructed based on known inducible gene control elements. For example, inducible promoters may be constructed by combining an element responsive to a drug or hormone which may be administered in the diet. In a preferred embodiment, a human oestrogen responsive element (ERE) may be used to regulate expression of the protein of interest, as long as the insect is transformed with a second coding sequence which expresses the human oestrogen receptor.

Constitutive promoters may also be used to express the protein of interest and/or other proteins required in the insect larva. For example, the constitutive promoter may be a cytoplasmic actin promoter. The *D. Melanogaster* cytoplasmic actin promoter has been cloned (Act5C) and is highly active in mosquitoes (Huynh and Zieler, (1999) J. Mol. Biol. 288:13–20). Cytoplasmic actin genes and their promoters may also be isolated from other insects, including medfly.

Other examples include the cytoplasmic tubulin promoter, for instance the medfly cytoplasmic tubulin promoter.

Promoters which control secreted polypeptides may be used, optionally together with appropriate signal sequences, to direct secretion of the protein to the haemolymph. For example, the larval serum protein promoter may be employed (Benes et al., (1995) Mol. Gen. Genet 249(5): 545–56).

Rearing of Larvae

Mass rearing technology for medfly is highly developed. Mass rearing facilities exist that produce over 1,000 million flies per week. These flies are used for medfly pest control by the sterile insect technique: they are steriuised by exposure to radiation at the pupal stage and then released.

The life cycle of the medfly is about 25 days at 25° C. and a female normally lays 100–200 eggs. As all holometabolous insects, the medfly has four distinct developmental stages: Embryonic (lasts about 2 days), larval (about 8 days). pupal (about 10 days) and adult. Sexual maturity is attained within 4–6 days of adult life. Just before pupariation, each larva is about 10 mg in mass and contains approximately 200 micrograms of protein.

For protein production, larval cultures that have been initiated at different times can be synchronised by appropriate temperature shift regimes. This is possible because growth rates depend on the temperature of the environment; at 18° C. larval growth rates decrease by approximately 50%.

For laboratory scale production, the use of smaller insects such as *Drosophila* is preferred. Although less protein is produced per larva, the life cycle is shorter and production may be established more rapidly. For instance, the life cycle of *Drosophila* is 12 days, with 1 mg larvae capable of each yielding 20 µg of protein.

The invention is described, for the purposes of illustration only, in the following examples.

EXAMPLES

Example 1

Production of GFP in Medfly and *Drosophila* Larvae

The gene encoding Green Fluorescent Protein from the jellyfish *Aequoria victoria* has been expressed in the medfly, *Ceratitis capitata*, and in the fruitfly *Drosophila melanogaster*. Transgenic *Drosophila* and medfly larvae, pupae and adults containing single and multiple insertions of a Minos/GFP transposon in their genome show GFP-characteristic fluorescence. Two GFP constructs are used, one with an inducible promoter (the *Drosophila* Hsp70) and one with a constitutive promoter (the *Drosophila* actin5C promoter). *Drosophila* and medfly Larvae with the Hsp70/GFP gene show low levels of fluorescence at the normal rearing temperature (22 degrees C.) and elevated fluorescence after exposure for 1 hr at an elevated temperature (39 degrees C.). *Drosophila* larvae with the actin5C/GFP gene show constitutive high levels of GFP fluorescence. GFP is expressed in most, if not all tissues of *Drosophila* and medfly. GFP protein is also detected in transgenic insects using an immunoblot assay. Comparison of several transgenic lines showed that levels of GFP expression depend on the position of integration of the transgene and on the number of transgene copies present in the genome.

Materials and Methods

Flies and DNA injection: The *Drosophila* yw strain and the *Ceratitis capitata* strain A71, a white-eves strain homozygous for the w1 gene, are used in all experiments; flies are reared at 22 degrees C. under standard conditions. DNA injections of transposon plasmids along with a helper plasmid expressing transposase are performed using pre-blastoderm embryos as previously described (Loukeris et al 1995, Science).

Plasmid Constructions and DNA Analysis:

Plasmid pMiHsp70/GFP is constructed by inserting a PCR-amplified fragment containing the GFP gene into the multiple cloning site of plasmid pHSS6Hsp70PT, in the appropriate orientation. Plasmid pHSS6Hsp70PT contains, in the appropriate orientations, the promoter and the 3' mRNA trailer—polyadenylation signal (hereinbelow called 'terminator') of the Hsp70 gene of *Drosophila melanogaster*. Promoter and terminator are separated by a multiple cloning site. The Hsp70 promoter also contains the 5' untranslated leader sequence of the Hsp70 mRNA for increased mRNA stability. The promoter/GFP/terminator cassette is then cloned as a NotI fragment into a Minos vector, containing the wild-type cDNA of the Medfly white gene (Loukeris et al., 1995, Science). The white gene is used as a primary visible genetic marker for detection of transformants (Loukeris et al., 1995, Science). The structure of the pMiHspGFP/HspCcW transposon is shown in FIG. 1.

Figure 2:
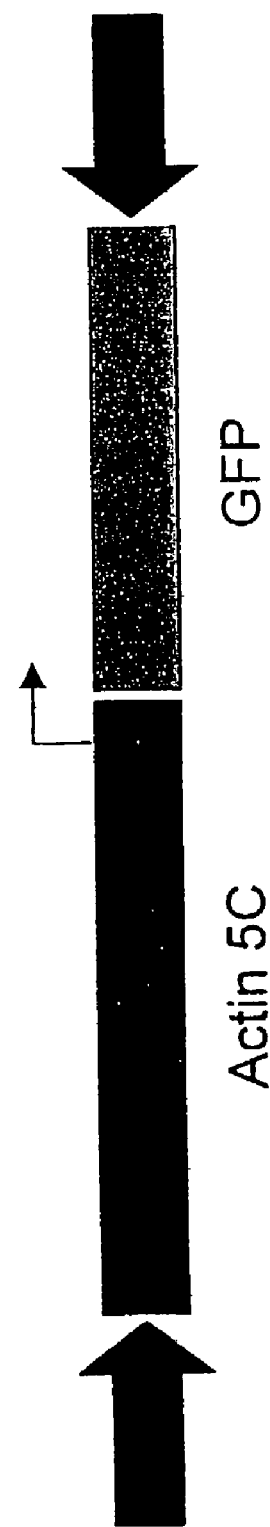
FIG. 2 shows the structure of plasmid pMiAct5CGFP which expresses GFP under the control of the Drosophila Actin 5C gene.

Plasmid pMiAct5CGFP (FIG. 2) contains the GFP gene downstream of the *Drosophila melanogaster* 2 kb fragment containing the promoter of the Actin5C gene, which encodes ubiquitously expressed cytoplasmic actin. Plasmid pMiAct5CGFP does not contain the white gene as a primary marker, and transformants generated with this plasmid are identified on the basis of GFP expression only (see below).

In a typical transgenesis experiment, a mixture of transposon plasmid DNA and helper plasmid DNA are co-injected into pre-blastoderm (0–1 hour post-oviposition) *Drosophila* or medfly embryos homozygous for the eye colour mutation white. To detect transgenic medfly, the flies derived from injected embryos (generation G0) are bred by back-crossing to the recipient strain and their progeny are tested individually at the larval stage for expression of either the white gene (flies injected with pMiHspGFP/HspCcW) or GFP (flies injected with pMiAct5CGFP). Expression of white is detectable as a change of eye colour from white to coloured (varying form pale yellow to wild-type red). Expression of GFP is monitored by detecting GFP-specific fluorescence in the tissues of larvae after two successive 1-hour heat treatments of larvae at 39° C. separated by one day, using standard epifluorescence microscopy.

Individual transgenic larvae (generation G1) are bred by back-crossing to the recipient strain and individual white or GFP-expressing progeny (G2) are inter-bred to produce homozygous progeny (G3). Intensity of eye colour or of GFP fluorescence is dependent on gene dosage. Homozygous individuals are detected, therefore, among the G3 progeny by following these phenotypes. Putative homozygous G3 individuals are interbred and their progeny is analysed by Southern blotting to determine whether they contain single or multiple insertions. Strains homozygous for single insertions are established by this procedure.

Heat-Inducible Expression of GFP in *Drosophila* and Medfly Larvae

Figure 3:
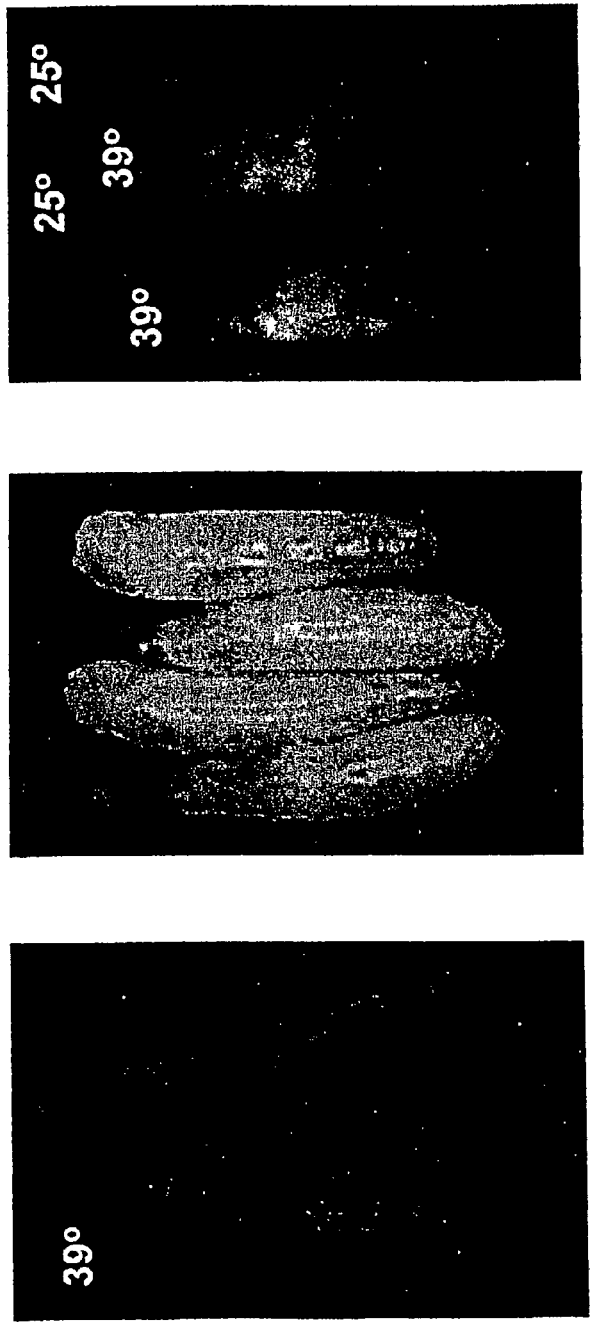
FIG. 3 shows the expression of GFP in transgenic medfly and medfly larvae after heat shock.

Transgenic *Drosophila* and medfly larvae homozygous for insertions of the MiHspGFP/HspCcW transposon grown at the standard temperature of 22–24 degrees C. show low but detectable levels of GFP fluorescence compared with non-transgenic larvae. Fluorescence increases dramatically after heat shock (FIG. 3).

Constitutive Expression of GFP in *Drosophila*

Figure 4:
FIG. 4 shows constitutive expression of GFP in Drosophila flies.
Figure 5:
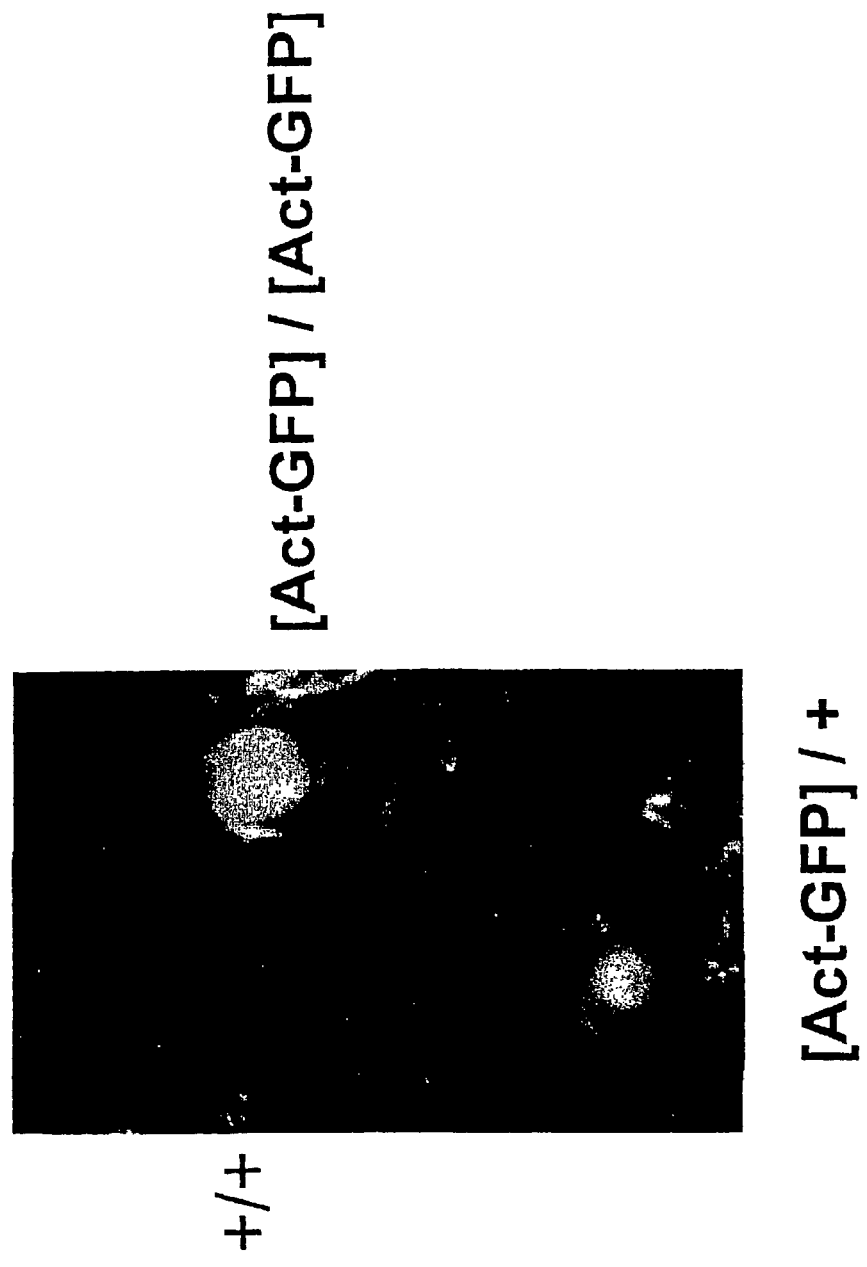
FIG. 5 shows the constitutive expression of GFP in adult Drosophila. The fluorescence, observed is gene dose-dependent.
Figure 6:
FIG. 6 shows the expression of GFP in Drosophila larvae (top: transgenic; bottom: wildtype)

Transgenic *Drosophila* homozygous for insertions of the transposon MiAct5CGFP grown at the standard temperature of 22–24 degrees C. show high levels of GFP fluorescence compared with non-transgenic in adult flies (FIG. 4) and in larvae (FIG. 6). The levels of fluorescence are gene dose dependent (FIG. 5).

No GFP-expressing medfly are detected in the progeny of more than 1000 G0's injected with MiAct5CGFP. We conclude that the *Drosophila* actin5C promoter is a weak promoter in medfly and that a homologous actin promoter will have to be used in medfly to achieve high levels of constitutive expression of heterologous proteins.

Several *Drosophila* transgenic lines homozygous for MiAct5CGFP are compared to each other for expression of GFP. Although all lines demonstrated high levels of fluorescence, line-specific differences in intensity are detectable.

Example 2

Production Of Human Growth Hormone In Medfly Larvae

A cDNA sequence encoding hGH is cloned downstream of the *D. melanogaster* promoter for the Hsp70 heat shock gene. The Hsp70 promoter also contains the 5' untranslated leader sequence of the Hsp70 mRNA for increased mRNA stability. The *D. melanogaster* Hsp70 3' untranslated trailer, containing a polyadenylation signal, is cloned downstream of the hGH encoding sequence. The construct is inserted in a Minos vector also containing a marker construct. The marker construct consists of the Green Fluorescent Protein (GFP) gene from *Aequoria victoria* driven by the *D. melanogaster* Hsp70 promoter and also containing the Hsp70 3' region. This marker confers a visible genotype (GFP fluorescence) to transgenic organisms and is used for detecting transgenic medfly at the embryonic, larval, or adult stage. The overall structure of the complete transposon is, therefore:

Minos left inverted repeat—hGH expressing construct—GFP marker expressing construct—Minos right inverted repeat.

The transposon is constructed in *E. coli* in a BlueScript vector.

In vitro synthesised mRNA encoding Minos transposase is used as a transposase source in transgenesis experiments. The mRNA is synthesised in vitro using as a template an expression vector plasmid containing the transposase gene cloned downstream from a phage T7 promoter and commercially-available T7 RNA polymerase. The complete uninterrupted DNA sequence encoding Minos transposase is obtained by reverse transcription of the Minos mRNA from transgenic *D. melanogaster* expressing Minos transposase.

Plasmid DNA containing the transposon is co-injected with Minos transposase mRNA into pre-blastoderm (0–1 hour post-oviposition) embryos. Conditions for medfly embryo handling and injection have been described in the literature (Loukeris et al. 1995). Under these conditions, 10–20% of fertile flies derived from the injected embryos are expected to give transgenic progeny. To detect transgenic medfly, the files derived from injected embryos (generation G0) are bred by back-crossing to the recipient strain, and their progeny are tested individually at the larval stage for expression of GFP. This is done by detecting GFP-specific fluorescence in the tissues of larvae after two successive 1-hour treatments at 39° C., separated by one day, using standard epifluorescence microscopy.

Individual transgenic larvae (generation G1) are bred by back-crossing to the recipient strain and individual GFP-expressing progeny (G2) are inter-bred to produce homozygous progeny (G3). Homozygous G3 individuals are detectable by measuring GFP expression by quantitative epifluorescence microscopy. Strains homozygous for single insertions are established.

In such transgenic strains, levels of transgene expression depend not only on the promoter and on conditions of induction, but also on the point of transgene insertion. Several independently obtained strains (i.e., strains derived from different G0 flies) are tested for levels of hGH expression and those showing the highest levels are characterised further at the molecular and cytogenic levels. Molecular characterisation consists of Southern analysis and, for strains that will eventually be used for protein production, cloning and sequencing of the transgene. Cytogenic characterisation is done by in situ hybridisation on salivary gland polytene chromosomes to determine the chromosomal point of insertion.

To construct strains with multiple insertions, appropriate crosses are performed between members of different strains. The progeny of these crosses are inter-bred and multiply homozygous individuals recovered using GFP as a marker. Depending on the chromosomal position of insertions, strains carrying balancer chromosomes can be used to facilitate these constructions. Three to four generations are required for constructing stable strains with multiple insertions.

Mass rearing of larvae is carried out according to established procedures. Larvae are reared on a semi-dry food consisting of a bran base supplemented with yeast. Larval growth is synchronised by appropriate temperature shifts and third-instar Larvae treated at 39–41° C. for the time required for maximal induction of the transgene. Late third instar larvae move away from food, in search of a place to pupariate. This behaviour is used to harvest larvae from the food for mass fly production in mass rearing facilities; it is also applied to the harvesting of food-free larvae for protein production and purification.

Medfly larvae are washed with chilled saline and then homogenised in the presence of protease inhibitors, hGH is purified from the homogenate according to standard procedures.

Example 3

Production of a Camelid Antibody in Medfly Larvae

Figure 7:
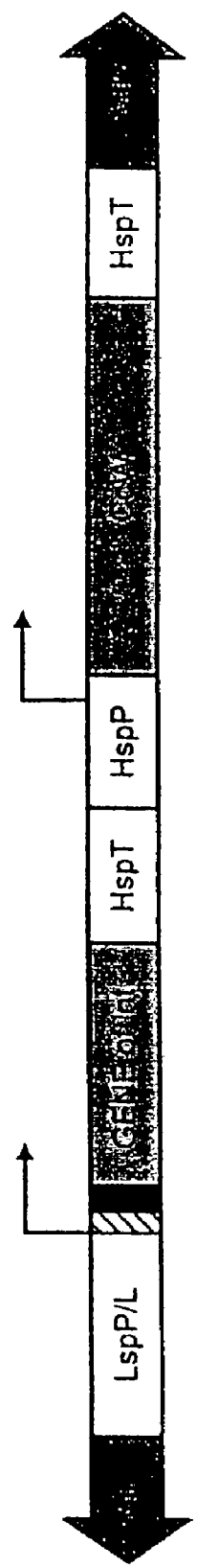
FIG. 7 shows the structure of a vector for expression of a protein in larval haemolymph. LspP/L is the promoter of Drosophila or Medfly Larval Serum Protein (Lsp) gene, followed by the Lsp 5' untranslated leader (striped box) and the Lsp signal peptide (black box). The gene of interest is fused in frame to the leader peptide. HspP and HspT are heat shock 70 gene promoter and terminator, respectively. CcW is the medfly white gene, used as a dominant visible marker for detecting transformants. MiL and MiR are the ends of the Minos element.

A vector designed for expression of a protein in larval haemolymph is shown in FIG. 7. LspP/L is the promoter of Drosophila or Medfly Larval Serum Protein (Lsp) gene (Benes et al., (1995) Mol. Gen. Genet. 249(5):545–56), followed by the Lsp 5' untranslated leader (striped box) and the Lsp signal peptide (black box). The gene of interest, in this case the camelid antibody gene, is fused in frame to the leader peptide. HspP and HspT are heat shock 70 gene promoter and terminator, respectively. CcW is the medfly white gene, used as a dominant visible marker for detecting transformants. MiL and MiR are the ends of the Minos element.

A camelid antibody is isolated from a phage expression library (Unilever). The antibody is specific for the porcine retrovirus PERV (porcine endogenous retrovirus) and recognises the p30 component of the PERV gag proteins (the viral core proteins). A p30 clone is expressed in the expression vector pHEN1 in order to obtain antigen for screening the antibody library, and antibody clones selected accordingly. A preliminary sequence and translation of the antibody used in this experiment is set forth in FIG. 8.

Transgenic flies are identified by white expression as in Example 1. Antibody expression is detected in the haemolymph of transgenic fly larvae.

Antibody is purified by homogenising larval extract and purification by Protein A column chromatography. Immunoglobulins bind to Protein A at pH 8.6 and elute from the column at pH 4.3. Thus elution is done by lowering the pH of the Protein A column. Protein A agarose (0.25 g; Sigma) is swollen in Tris-buffered saline (0.05 M Tris 0.15 M NaCl, pH 8.6) and then packed into a column (the bed volume is 1 ml). The culture supernatant is adjusted to pH 8.6 by adding dilute NaOH and is then centrifuged at 600 g for 30 min at 4° C. After the sample is loaded, the Protein A column is washed with Tris-buffered saline, pH 8.6, until no proteins are eluted from the column. Then, step elutions are carried out with PBS (0.05 M phosphate/0.15 M NaCl, pH 7.0), citrate-buffered saline (0.05 M citrate/0.15 M NaCl, pH 5.5) and acetate-buffered saline (0.05 M acetate/0.15 M NaCl, pH 4.3) until the antibody is eluted. Fractions contributing to the peak of A 280 are pooled, dialysed in 0.01×PBS, lyophilised, redissolved in 500 μl of PBS and stored at −70° C. The purity of the protein peak is analysed by SDS/PAGE. The column is regenerated by washing with glycine-buffered saline (0.05 M glycine/HCl/0.15 M NaCl, pH 2.3) followed by Tris-buffered saline (pH 8.6, containing 0.02% $NaN_3$).

An ELISA assay is performed using immobilised p30 antigen, produced as above, and a labelled murine anti-camelid monoclonal antibody. The specificity of the antibody eluted from medfly larvae for PERV p30 is thus confirmed.

Example 4

Production of Human α-Glucosidase in Medfly Larvae

A heat-shock inducible transposon expression system in accordance with Example 1 is constructed, using the human α-glucosidase gene (GenBank GI:182907) in place of the GFP gene.

A mixture of transposon plasmid DNA and helper plasmid DNA, as per Example 1 is co-injected into pre-blastoderm (0–1 hour post-oviposition) Drosophila or medfly embryos homozygous for the eye colour mutation white. To detect transgenic medfly the flies derived from injected embryos (generation G0) are bred by back-crossing to the recipient strain, and their progeny are tested individually at the larval stage for expression of the white gene. Expression of white is detectable as a change of eye colour from white to coloured (varying form pale yellow to wild-type red).

Individual transgenic larvae (generation G1) are bred by back-crossing to the recipient strain and individual white progeny (G2) are inter-bred to produce homozygous progeny (G3). Intensity of eye colour is dependent on gene dosage. Homozygous individuals are detected, therefore, among the G3 progeny by following these phenotypes. Putative homozygous G3 individuals are interbred and their progeny is analysed by Southern blotting to determine whether they contain single or multiple insertions. Strains homozygous for single insertions are established by this procedure.

Heat-Inducible Expression of α-Glucosidase in *Drosophila* and Medfly Larvae

Transgenic *Drosophila* and medfly larvae homozygous for insertions of the MiHsp α-glucosidase/Hsp(6W) transposon grown at the standard temperature of 22–24 degrees C. show low but detectable levels of α-glucosidase compared with non-transgenic larvae in the fat pads, as assessed by immunoquantification according to Umapathysivam et al., Clin Chem 2000 46(9):1318–25. The amount of α-glucosidase increases markedly after heat shock.

The invention claimed is:

1. A method for producing milligram quantities of a protein of interest for research purposes, comprising:
   (a) providing an insect transformed with a functional gene encoding the protein of interest by injecting an egg or embryo of an insect with a transposon dependent non-viral DNA vector system comprising a gene encoding the protein of interest flanked by terminal repeats of a transposon, said egg or embryo comprising a transposase protein active on said terminal repeats in said insect, wherein the gene encoding said protein of interest is excised from the non-viral DNA vector by the transposase protein and inserted into the host insect chromosomal DNA;
   (b) identifying and selecting the progeny of the transformed insect that carry the recombinant transposed gene of interest in their germline;
   (c) breeding said progeny identified in step (b) to produce larvae;
   (d) mass rearing a sufficient number of said larvae to produce milligram quantities of said protein of interest; and
   (e) extracting said protein of interest from the mass reared larvae.

2. A method for producing kilogram quantities of a protein of interest for clinical and diagnostic applications comprising:
   (a) providing an insect transformed with a functional gene encoding the protein of interest by injecting an egg or embryo with a transposon dependent non-viral DNA vector system comprising a gene encoding the protein of interest flanked by terminal repeats of a transposon, said egg or embryo comprising and a transposase protein active on said terminal repeats in said insect, wherein the gene encoding said protein of interest is excised from the non-viral DNA vector by the transposase protein and inserted into the host insect chromosomal DNA;
   (b) identifying and selecting the progeny of the transformed insect that carry the recombinant transposed gene of interest in their germline;
   (c) breeding said progeny identified in step (b) to produce larvae;
   (d) mass rearing a sufficient number of said larvae to produce kilogram quantities of said protein of interest; and
   (e) extracting said protein of interest from the mass reared larvae.

3. A method for producing kilogram quantities of a protein of interest wherein said protein of interest is an industrial enzyme comprising:
   (a) providing an insect transformed with a functional gene encoding the protein of interest by injecting an egg or embryo with a transposon dependent non-viral DNA vector system comprising a gene encoding the protein of interest flanked by terminal repeats of a transposon, said egg or embryo comprising a transposase protein active on said terminal repeats in said insect, wherein the gene encoding said protein of interest is excised from the non-viral DNA vector by the transposase protein and inserted into the host insect chromosomal DNA;
   (b) identifying and selecting the progeny of the transformed insect that carry the recombinant transposed gene of interest in their germline;
   (c) breeding said progeny identified in step (b) to produce larvae;
   (d) mass rearing a sufficient number of said larvae to produce kilogram quantities of said protein of interest; and
   (e) extracting said protein of interest from the mass reared larvae.

4. A method for producing kilogram quantities of a protein of interest for dietary or pharmaceutical use comprising:
   (a) providing an insect transformed with a functional gene encoding the protein of interest by injecting an egg or embryo with a transposon dependent non-viral DNA vector system comprising a gene encoding the protein of interest flanked by terminal repeats of a transposon, said egg or embryo comprising a transposase protein active on said terminal repeats in said insect, wherein the gene encoding said protein of interest is excised from the non-viral DNA vector by the transposase protein and inserted into the host insect chromosomal DNA;
   (b) identifying and selecting the progeny of the transformed insect that carry the recombinant transposed gene of interest in their germline;
   (c) breeding said progeny identified in step (b) to produce larvae;
   (d) mass rearing a sufficient number of said larvae to produce kilogram quantities of said protein of interest; and
   (e) extracting said protein of interest from the mass reared larvae.

5. The method according to claim 1, 2, 3 or 4, wherein said transposase protein is encoded by a transposable element selected from the group consisting of Minos, mariner, Hermes, sleeping beauty and piggyBac.

6. The method according to claim 1, 2, 3 or 4, wherein said gene encoding a protein of interest, is under the control of a constitutive transcriptional control element which is operative in said insect larvae.

7. The method according to claim 6, wherein said transcriptional control element is a heat shock promoter, or is regulatable by tetracycline; or regulatable by oestrogens.

8. The method according to claim 1, 2, 3 or 4, wherein said gene encoding a protein of interest, is under the control of a constitutive transcriptional control element which is operative in said insect larvae.

9. The method according to claim 1, 2, 3 or 4, wherein said protein of interest is accumulated primarily in the fat bodies or the haemolymph of said larvae.

10. The method according to claim 9, wherein a signal peptide is operatively linked to the protein of interest and directs the secretion of the protein of interest into the haemolymph.

11. The method according to claim 1, 2, 3 or 4, wherein said insect is transformed with two or more genes encoding a protein of interest.

12. The method according to claim 1, 2, 3, or 4, wherein said protein of interest is selected from the group consisting of an enzyme, a cytokine, a hormone and a proteinaceous pharmaceutical.

13. The method according to claim 1, 2, 3 or 4, wherein the insect is selected from the group consisting of *Drosophila melanogaster, Bactrocera oleae* (olive fly), *Bactrocera orientalis* (oriental fruit fly), *Heliothis armigera* (cotton boliworm), *Trichoplusa ni* (cabbage looper), *Manduca sexta* (tobacco homworm), *Lobesia botrana* (grapevine moth), *Anopheles gambiae* (mosquito), *Aedes aegypti* (yellow fever mosquito), *Glossina morsitans* (tse-tse fly), *Simulium* sp. (black fly), *Phiebotomus* sp. (sand fly), *Musca domestica* (house fly) and *Ceratitis capitata* (Medfly).

14. The method according to claim 1, 2, 3 or 4, wherein said larvae of step (c) are synchronised by manipulation of culture temperatures.

15. The method according to claim 1, 2, 3 or 4, wherein said transformed insect is transformed with a transposon dependent non-viral DNA vector system comprising one or more genes, wherein each gene encodes a protein of interest, and wherein said one or more genes are flanked by terminal repeats of a transposon and the gene is excised from the vector and inserted into the insect chromosomal DNA by said transposase protein.

16. The method of claim 1, 2, 3 or 4, wherein said transformed insect is produced by:
  providing a DNA plasmid comprising a gene encoding a protein of interest flanked by terminal repeats of a transposon, wherein said DNA plasmid expresses said protein of interest in the larvae of said transformed insect;
  providing a transposase protein which is active on said terminal repeats in said insect; and
  injecting an egg or embryo of an insect with said DNA plasmid in the presence of said transposase protein, and wherein the gene encoding the protein of interest is excised from the DNA plasmid by said transposase protein and inserted into the host chromosomal DNA, to produce said transformed insect.

17. The method of claim 1, 2, 3 or 4, further comprising the step of selecting and establishing transformed insect lines, prior to step (d).

18. The method of claim 1, 2, 3, or 4 wherein said egg or embryo is injected with an mRNA encoding said transposase protein.

19. The method of claim 1, 2, 3 or 4, wherein said egg or embryo is injected with a plasmid expressing said transposase protein.

20. The method of claim 1, 2, 3, or 4, wherein said egg or embryo is injected with said transposase protein.

21. The method of claim 1, 2, 3 or 4, wherein said protein of interest is an antibody.

* * * * *